(12) United States Patent
Tomioka

(10) Patent No.: US 8,859,970 B2
(45) Date of Patent: Oct. 14, 2014

(54) TERAHERTZ WAVE GENERATING DEVICE, CAMERA, IMAGING DEVICE, AND MEASUREMENT DEVICE

(75) Inventor: Hiroto Tomioka, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 234 days.

(21) Appl. No.: 13/494,240

(22) Filed: Jun. 12, 2012

(65) Prior Publication Data

US 2012/0326036 A1 Dec. 27, 2012

(30) Foreign Application Priority Data

Jun. 24, 2011 (JP) .................................. 2011-141089

(51) Int. Cl.
*G01J 5/02* (2006.01)
*G01N 21/35* (2014.01)
*G01J 3/28* (2006.01)
*G02F 2/02* (2006.01)
*G01J 3/10* (2006.01)

(52) U.S. Cl.
CPC ............... *G01J 3/10* (2013.01); *G02F 2203/13* (2013.01); *G01N 21/3581* (2013.01); *G01J 3/2823* (2013.01); *G02F 2/02* (2013.01)

USPC ......................................................... 250/341.1

(58) Field of Classification Search
CPC .................................................. G01N 21/3581
USPC ......................................................... 250/341.1
See application file for complete search history.

(56) References Cited

U.S. PATENT DOCUMENTS

| | | | | |
|---|---|---|---|---|
| 6,348,683 | B1 * | 2/2002 | Verghese et al. | ........... 250/214.1 |
| 7,174,037 | B2 * | 2/2007 | Arnone et al. | ............... 382/128 |
| 7,884,942 | B2 * | 2/2011 | Umetsu | ........................ 356/445 |

FOREIGN PATENT DOCUMENTS

JP 2006-010319 A 1/2006

* cited by examiner

*Primary Examiner* — Constantine Hannaher
(74) *Attorney, Agent, or Firm* — Global IP Counselors, LLP

(57) ABSTRACT

A terahertz wave generating device includes a first light source, a second light source and an antenna. The first light source and a second light source are configured and arranged to generate pulsed lights. The antenna is configured and arranged to generate terahertz waves when irradiated by the pulsed lights generated by the first light source and the second light source. The antenna has a pair of electrodes arranged opposite each other with a gap being formed therebetween. The first light source and the second light source are configured and arranged to irradiate the pulsed lights between the electrodes at timings that are offset from each other.

13 Claims, 13 Drawing Sheets

… (1) …

TERAHERTZ WAVE GENERATING DEVICE, CAMERA, IMAGING DEVICE, AND MEASUREMENT DEVICE

CROSS-REFERENCE TO RELATED APPLICATIONS

This application claims priority to Japanese Patent Application No. 2011-141089 filed on Jun. 24, 2011. The entire disclosure of Japanese Patent Application No. 2011-141089 is hereby incorporated herein by reference.

BACKGROUND

1. Technical Field

The present invention relates to a terahertz wave generating device, a camera, an imaging device, and a measurement device.

2. Related Art

In recent years, attention has been devoted to terahertz waves, which are electromagnetic waves having frequencies equal to or larger than 100 GHz and smaller than and equal to 30 THz. Terahertz waves can be used, for example, in such applications as imaging, spectrometry and other measurement techniques, and non-destructive testing. A terahertz wave generating device that generates such terahertz waves has a light source device that generates light pulses (pulsed light) having a sub-picosecond pulse width (several hundred femtoseconds) and an antenna that that generates terahertz waves when irradiated with the light pulses generated by the light source device (e.g., see Japanese Laid-Open Patent Publication No. 2006-10319). A conventional terahertz wave generating device is configured such that the light pulse from one light source device irradiated onto a space between one pair of electrodes of the antenna. However, the conventional terahertz wave generating device is disadvantageous in that it can only generate a terahertz wave having a prescribed frequency distribution.

SUMMARY

An object of the present invention is to provide a terahertz wave generating device, a camera, an imaging device, and a measurement device that can adjust the frequency distribution of the terahertz wave.

The object is achieved by the present invention described below. A terahertz wave generating device according to one aspect of the present invention includes a first light source, a second light source and an antenna. The first light source and a second light source are configured and arranged to generate pulsed lights. The antenna is configured and arranged to generate terahertz waves when irradiated by the pulsed lights generated by the first light source and the second light source. The antenna has a pair of electrodes arranged opposite each other with a gap being formed therebetween. The first light source and the second light source are configured and arranged to irradiate the pulsed lights between the electrodes at timings that are offset from each other. In this way, the frequency distribution of the terahertz waves can be adjusted easily and reliably.

In the terahertz wave generating device according to the above described aspect of the present invention, an amount by which irradiation timings of the pulsed lights are preferably offset from each other is smaller than a pulse width of each of the pulsed lights. In this way, the frequency distribution of the terahertz waves can be adjusted easily and reliably. In the terahertz wave generating device according to the above described aspect of the present invention, each of the first light source and the second light source is preferably a semiconductor laser. In this way, a small, simple terahertz wave generating device can be provided. In the terahertz wave generating device according to the above described aspect of the present invention, the first light source and the second light source are preferably provided as an integral unit. In this way, size of the terahertz wave generating device can be reduced.

A terahertz wave generating device according to another aspect of the present invention includes a first light source, a second light source, a third light source, a fourth light source, and an antenna. The first light source, a second light source, a third light source, and a fourth light source are configured and arranged to generate pulsed lights. The antenna is configured and arranged to generate terahertz waves when irradiated by the pulsed lights generated by the first light source, the second light source, the third light source, and the fourth light source. The antenna has a first pair of electrodes and a second pair of electrodes, the electrodes of each of the first and second pairs being arranged opposite each other with a gap being formed therebetween. The first light source and the second light source are configured and arranged to irradiate the pulsed lights between the electrodes of the first pair at timings that are offset from each other. The third light source and the fourth light source are configured and arranged to irradiate the pulsed lights between the electrodes of the second pair at timings that are offset from each other. A phase of at least one of the pulsed light emitted from the first light source and the pulsed light emitted from the second light source and a phase of at least one of the pulsed light emitted from the third light source and the pulsed light emitted from the fourth light source are different. In this way, the frequency distribution of the terahertz waves can be adjusted easily and reliably and an emission direction of the terahertz waves can be changed.

In the terahertz wave generating device according to the above described aspect of the present invention, an amount by which irradiation timings of the pulsed lights irradiated between the electrodes of the first pair are preferably offset from each other is smaller than a pulse width of each of the pulsed lights, and an amount by which irradiation timings of the pulsed lights irradiated between the electrodes of the second pair are preferably offset from each other is smaller than a pulse width of each of the pulsed lights. In this way, the frequency distribution of the terahertz waves can be adjusted easily and reliably.

In the terahertz wave generating device according to the above described aspect of the present invention, an amount of offset between the phase of the least one of the pulsed light emitted from the first light source and the pulsed light emitted from the second light source and the phase of the at least one of the pulsed light emitted from the third light source and the pulsed light emitted from the fourth light source is preferably smaller than a pulse width of each of the pulsed lights. In this way, the emission direction of the terahertz waves can be changed easily and reliably.

In the terahertz wave generating device according to the above described aspect of the present invention, each of the first light source, the second light source, the third light source, and the fourth light source is preferably a semiconductor laser. In this way, a small, simple terahertz wave generating device can be provided. In the terahertz wave generating device according to the above described aspect of the present invention, the first light source, the second light source, the third light source, and the fourth light source are preferably provided as an integral unit. In this way, size of the terahertz wave generating device can be reduced. In the terahertz wave generating device according to the above described aspect of the present invention, one of the electrodes of the first pair and one of the electrodes of the second pair are preferably electrically connected. In this way, simple terahertz wave generating device can be provided.

A camera according to another aspect of the present invention includes a terahertz wave generating device and a terahertz wave detecting device. The terahertz wave generating device is configured and arranged to generate terahertz waves. The terahertz wave detecting device is configured and arranged to detect the terahertz waves that have been emitted from the terahertz wave generating device and have penetrated through or been reflected from an object. The terahertz wave generating device includes a first light source, a second light source and an antenna. The first light source and a second light source are configured and arranged to generate pulsed lights. The antenna is configured and arranged to generate the terahertz waves when irradiated by the pulsed lights generated by the first light source and the second light source. The antenna has a pair of electrodes arranged opposite each other with a gap being formed therebetween. The first light source and the second light source are configured and arranged to irradiate the pulsed lights between the electrodes at timings that are offset from each other. In this way, a camera can be provided which exhibits the effects of the present invention.

An imaging device according to another aspect of the present invention includes a terahertz wave generating device, a terahertz wave detecting device and an image forming section. The terahertz wave generating device is configured and arranged to generate terahertz waves. The terahertz wave detecting device is configured and arranged to detect the terahertz waves that have been emitted from the terahertz wave generating device and have penetrated through or been reflected from an object. The image forming section is configured and arranged to form an image of the object based on a detection result of the terahertz wave detecting device. The terahertz wave generating device includes a first light source, a second light source and an antenna. The first light source and a second light source are configured and arranged to generate pulsed lights. The antenna is configured and arranged to generate the terahertz waves when irradiated by the pulsed lights generated by the first light source and the second light source. The antenna has a pair of electrodes arranged opposite each other with a gap being formed therebetween. The first light source and the second light source are configured and arranged to irradiate the pulsed lights between the electrodes at timings that are offset from each other. In this way, an imaging device can be provided which exhibits the effects of the present invention.

A measuring device according to another aspect of the present invention includes a terahertz wave generating device a terahertz wave detecting device and a measuring section. The terahertz wave generating device is configured and arranged to generate terahertz waves. The terahertz wave detecting device is configured and arranged to detect the terahertz waves that have been emitted from the terahertz wave generating device and have penetrated through or been reflected from an object. The measuring section is configured and arranged to measure the object based on a detection result of the terahertz detecting device. The terahertz wave generating device includes a first light source, a second light source and an antenna. The first light source and a second light source are configured and arranged to generate pulsed lights. The antenna is configured and arranged to generate the terahertz waves when irradiated by the pulsed lights generated by the first light source and the second light source. The antenna has a pair of electrodes arranged opposite each other with a gap being formed therebetween. The first light source and the second light source are configured and arranged to irradiate the pulsed lights between the electrodes at timings that are offset from each other. In this way, a measuring device can be provided which exhibits the effects of the present invention.

BRIEF DESCRIPTION OF THE DRAWINGS

Referring now to the attached drawings which form a part of this original disclosure.

DETAILED DESCRIPTION OF EXEMPLARY EMBODIMENTS

A terahertz wave generating device, a camera, an imaging device, and a measuring device according to the present invention will now be explained based on preferred embodiments shown in the appended drawings.

First Embodiment

Figure 1:
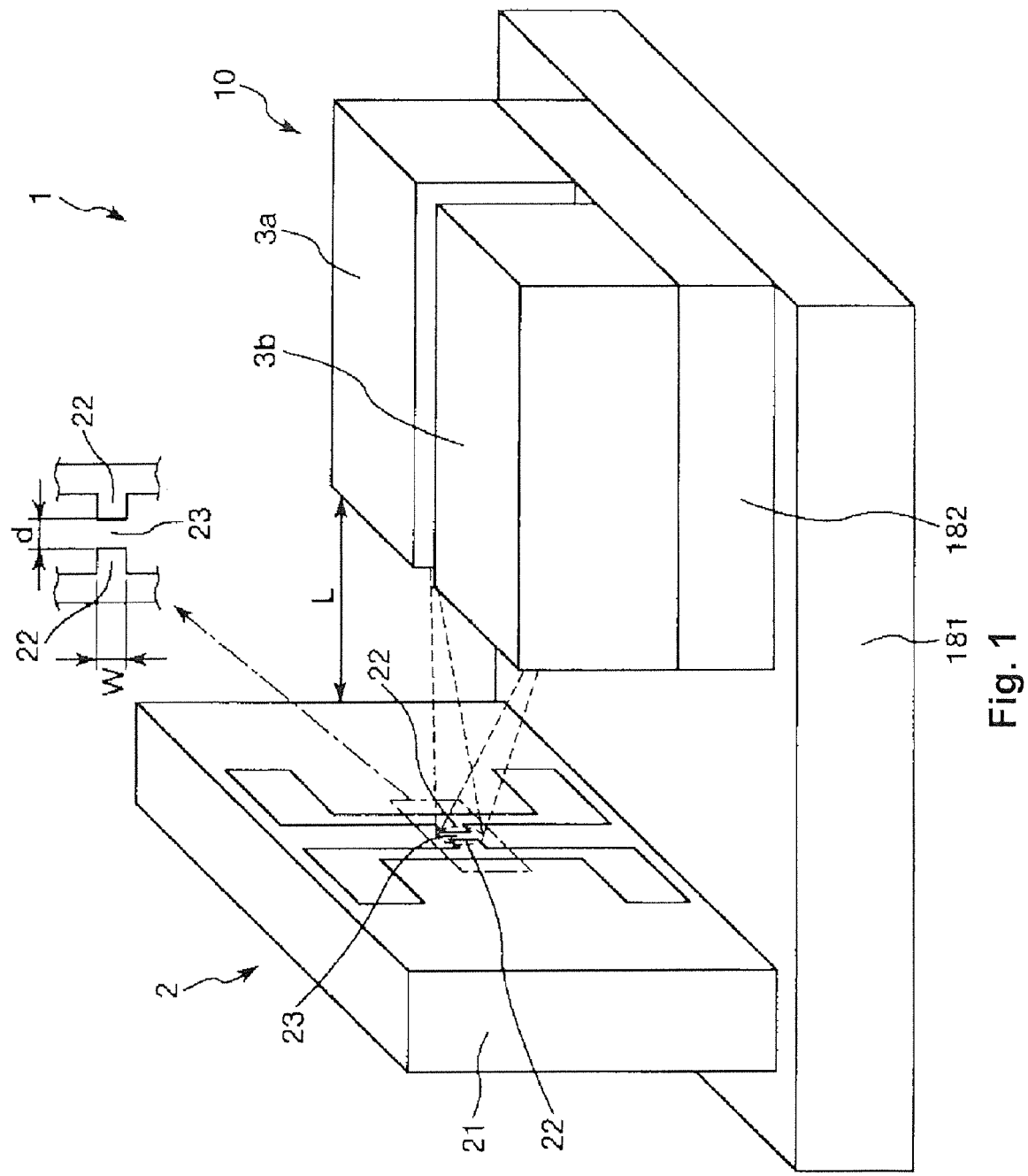
FIG. 1 is a perspective view schematically illustrating a first embodiment of a terahertz wave generating device according to the present invention.
Figure 2:
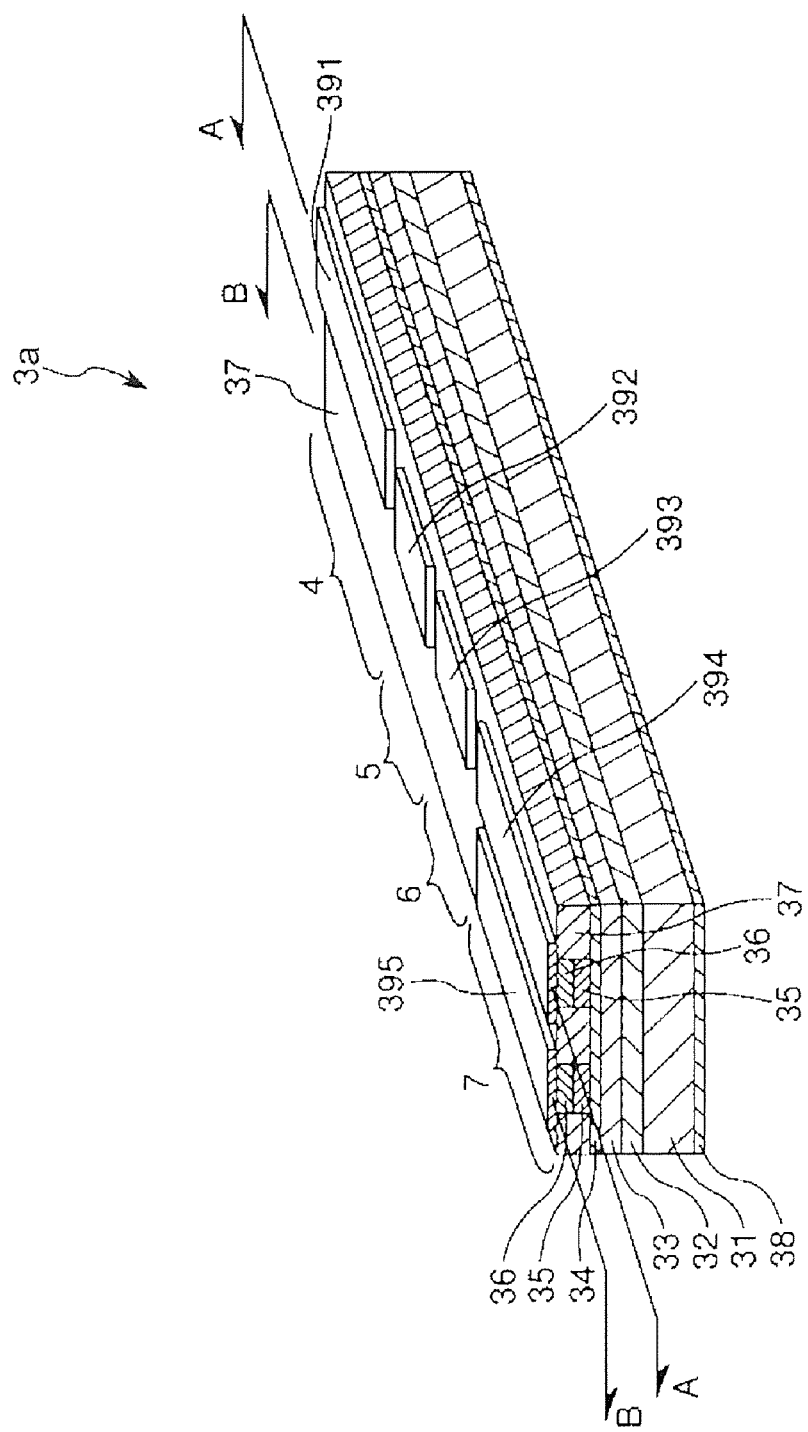
FIG. 2 is a sectional perspective view of a light source device of the terahertz wave generating device shown in FIG. 1.
Figure 3:
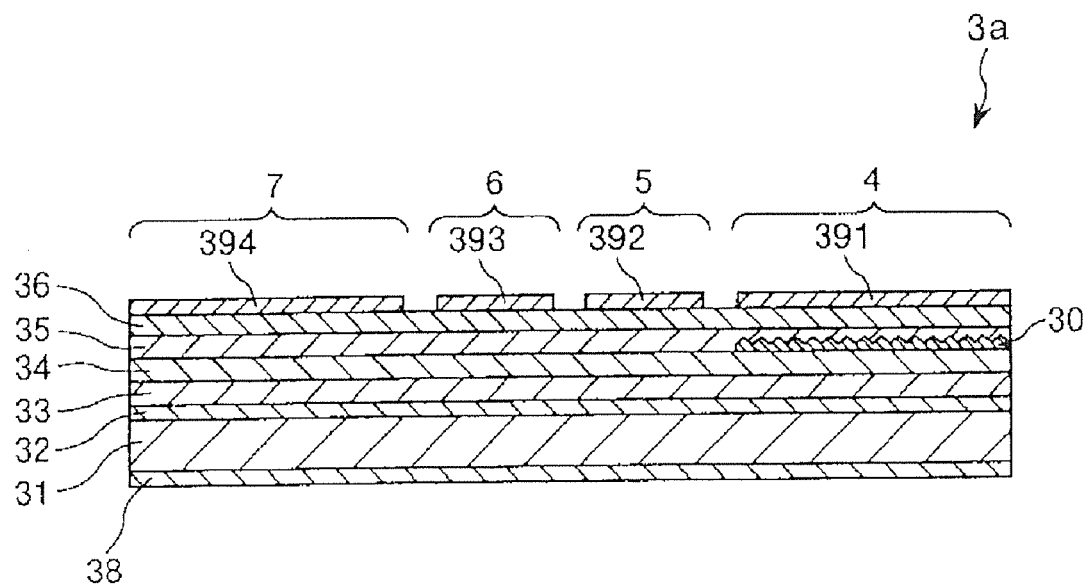
FIG. 3 is a sectional view taken along a section line A-A of FIG. 2.
Figure 4:
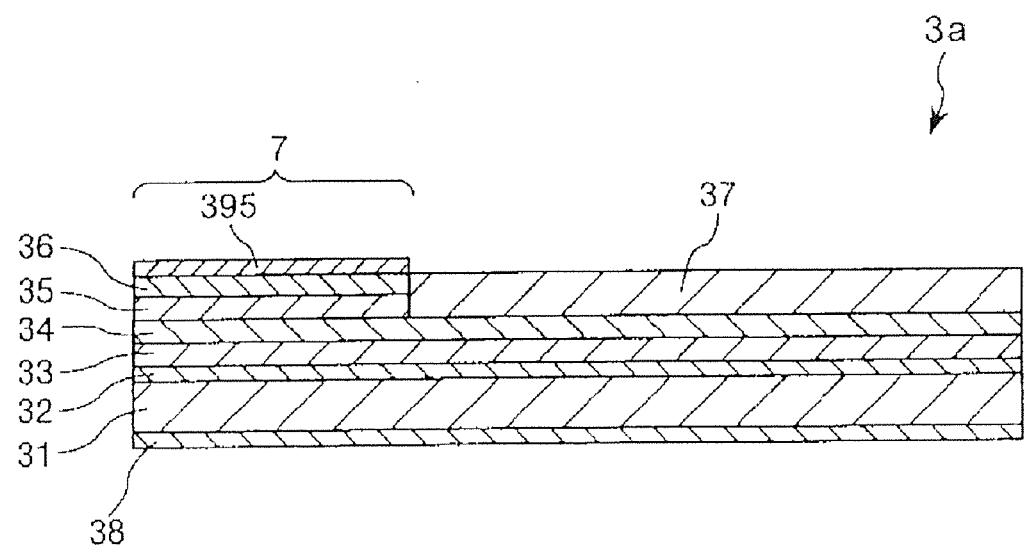
FIG. 4 is a sectional view taken along a section line B-B of FIG. 2.

FIG. 1 is a perspective view schematically illustrating a first embodiment of a terahertz wave generating device according to the present invention, FIG. 2 is a sectional perspective view of a light source device of the terahertz wave generating device shown in FIG. 1, FIG. 3 is a sectional view taken along a section line A-A of FIG. 2, and FIG. 4 is a sectional view taken along a section line B-B of FIG. 2. Also, in FIG. 1, a portion enclosed in a single-dot chain line is shown in an enlarged view.

As shown in FIG. 1, the terahertz wave generating device 1 comprises a light source unit 10 and an antenna 2. The light source unit 10 has a substrate 181, a sub-mount substrate 182 installed on the substrate 181, and two light source devices 3a and 3b installed side by side on the sub-mount substrate 182. The light source unit 10 generates two light pulses (pulsed lights) having different emission timings, i.e., different phases. The antenna 2 is installed on the substrate 181 and generates terahertz waves when irradiated with light pulses generated by the light source unit 10. There are no particular limitations on the shapes of the light pulses generated by the light source devices 3a and 3b; the shape of a single pulse is, for example, the shape of a single wave or rectangle. The light source device 3a constitutes a first light source, and the light source 3b constitutes a second light source.

In this embodiment, the antenna 2 is a dipole shaped semiconductor antenna (PCA) having a substrate 21 that is a semiconductor substrate and a pair of electrodes 22 that are provided on the substrate 21 and arranged to be separated by a gap 23. A voltage source (not shown) is connected between the two electrodes of the pair of electrodes 22, and a prescribed voltage is applied by the voltage source such that the antenna 2 generates a terahertz wave when a light pulse (pulsed light) is shown between the two electrodes 22. The terahertz wave is an electromagnetic wave having a frequency equal to or larger than 100 GHz and smaller than or equal to 30 THz, particularly a frequency equal to or larger than 300 GHz and smaller than or equal to 3 THz.

In the example shown in the figures, the shape of the substrate 21 is quadrilateral in a plan view. Also, the shape of the substrate 21 is not limited to a quadrilateral and such shapes as, for example, circular, elliptical, triangular, pentagonal, and hexagonal are also feasible. While there are no particular limitations on a distance d between the electrodes 22 and the distance d should be set as appropriate based on various conditions, the distance d is preferably equal to or larger than 1 μm and smaller than or equal to 10 μm.

While there are no particular limitations on a width w of the electrodes 22 and the width w should be set as appropriate based on various conditions, the width w is preferably equal to or larger than 1 μm and smaller than or equal to 10 μm. There are no particular limitations on the dimensions of the antenna 2 and the dimensions should be set as appropriate based on various conditions. However, the dimensions of the antenna 2 are preferably set such that one side dimension is equal to or larger than 100 μm and smaller than or equal to 10 mm and the other side dimension is equal to or larger than 100 μm and smaller than or equal to 10 mm. Furthermore, while there are no particular limitations on a distance L between a part where the light pulses of the light source unit 10 are emitted and the antenna 2 and the distance L should be set as appropriate based on various conditions, the distance L is preferably equal to or larger than 0.5 μm and smaller than or equal to 50 mm.

In this terahertz wave generating device 1, light pulses are irradiated from the light source device 3a and 3b of the light source unit 10 onto a space between a common pair of electrodes 22. Furthermore, the light pulses from the light source unit 10 are irradiated onto the space between the common pair of electrodes 22 at timings, i.e., phases, that are offset from each other. As a result, the frequency distribution of the terahertz waves generated by the antenna 2 is changed in comparison with a case in which the irradiation timings of the light pulses irradiated between the pair of electrodes 22 are not offset or a case in which a light pulse is only irradiated from one of the light sources 3a and 3b. That is, the frequency distribution of the terahertz waves generated by the antenna 2 can be adjusted.

The frequency distribution of the terahertz waves can be illustrated with a graph by, for example, indicating the frequency of the terahertz waves on a horizontal axis of the graph and indicating a magnetic field strength of the terahertz waves on a vertical axis. Then, for example, terahertz waves having a mountain-shaped frequency distribution when the irradiation timings of the light pulses irradiated between the pair of electrodes 22 are not offset can be changed to terahertz waves having a wave-shaped frequency distribution by offsetting the irradiation timings of the light pulses.

There are no particular limitations on the amount by which the timings of the light pulses are offset from each other and the amount of offset should be set as appropriate based on a targeted frequency distribution of the generated terahertz waves and various conditions. However, it is preferable for the offset amount to be smaller than the pulse width of the light pulses. More specifically, the offset amount of the irradiation timings of the light pulses is preferably set to an amount equal to or larger than 1% and smaller than or equal to 50% of the pulse width of the light pulses and still more preferably set to an amount equal to or larger than 3% and smaller than or equal to 40% of the pulse width of the light pulses. The pulse width of the light pulses is, for example, the width of the light pulse at half value when a single light pulse has the shape of a single wave and the full width of a single light pulse when the light pulses have a rectangular shape.

There are no particular limitations on a ratio $\alpha 1/\alpha 2$ of a peak value $\alpha 1$ of the intensity (wave height) of the light pulses generated by the light source device 3a with respect to a peak value $\alpha 2$ of the intensity of the light pulses generated by the light source device 3b, and this ratio should be set as appropriate based on a targeted frequency distribution of the generated terahertz waves and various conditions. However, it is preferable for the ratio to be equal to or larger than 1 and smaller than or equal to 10 and more preferably equal to or larger than 1 and smaller than or equal to 5.

Also, the terahertz wave frequency distribution can be adjusted by adjusting the offset amount of the irradiation timings of the optical pulses and by adjusting the ratio $\alpha 1/\alpha 2$ of the offset amount of the irradiation timings. The adjustment of the frequency distribution of the terahertz wave generating device 1 can be accomplished by experimentally determining a computational formula, table, or other form of analytical curve indicating a relationship between the offset amount of the irradiation timings and the frequency distribution of the terahertz waves or a computational formula, table, or detection amount indicating a relationship among the offset amount of the irradiation timings, the ratio $\alpha 1/\alpha 2$, and the frequency distribution of the terahertz waves and storing the analytical curve in a memory section (not shown) of the terahertz wave generating device 1. When necessary, the stored data is read and used.

A light source unit 10 will now be described. The light source unit 10 has a light source device 3a serving as a first light source and a light source device 3b serving as a second light source. Since the light source device 3a and the light source device 3b are the same, the light source device 3a will now be explained representatively. As shown in FIGS. 2 to 4, in this embodiment, the light source device 3a has a light pulse generator 4 that generates a light pulse, a first pulse compressor 5 that executes a pulse compression with respect to a light pulse generated by the light pulse generator 4, a second pulse compressor 7 that executes a pulse compression of the light pulse compressed by the first light pulse compressor 5, and an amplifier 6 that amplifies the light pulse.

The amplifier 6 can be provided upstream of the first pulse compressor 5 or between the first pulse compressor 5 and the second pulse compressor 7; in the example shown in the figure, the amplifier 6 is provided between the first pulse compressor 5 and the second pulse compressor 7. Thus, a light pulse compressed by the first pulse compressor 5 is amplified by the amplifier 6 and the light pulse amplified by the amplifier 6 is compressed by the second pulse compressor 7.

While there are no particular limitations on the pulse width (half-value width) of the light pulses emitted from the light source 3a, the pulse width is preferably equal to or larger than 10 fs and smaller than or equal to 800 fs. Also, a DBR laser, a DFB laser, a mode synchronizing layer, or other so-called semiconductor laser can be used as the light pulse generator 4. While there are no particular limits on the pulse width of the light pulses generated by the light pulse generator 4, the pulse width is preferably equal to or larger than 1 ps and smaller than or equal to 100 ps.

The first pulse compressor 5 executes pulse compression based on saturable absorption. That is, the first pulse compressor 5 has a saturable absorber that serves to compress light pulses such that the pulse width of the light pulses is decreased. The second pulse compressor 7 executes pulse compression based on a group velocity dispersion compensation. That is, the first pulse compressor 5 has a group velocity dispersion compensation medium, which in this embodiment is an optical coupling waveguide structure, that serves to compress light pulses such that the pulse width of the light pulses is decreased.

The light pulse generator 4 of the light source device 3a, the first pulse compressor 5, the amplifier 6, and the second pulse compressor 7 are combined as a unit, i.e., integrated onto a single substrate. More specifically, the light source device 3a has a semiconductor substrate 31, a clad layer 32 provided on the substrate 31, an active layer 33 provided on the clad layer 32, a waveguide formation process etching stop layer 34 provided on the active layer 33, a clad layer 35 provided on the waveguide formation process etching stop layer 34, a contact layer 36 provided on the clad layer 35, an insulating layer 37 provided on the waveguide formation process etching stop layer 34, an electrode 38 provided on the surface of the substrate 31 opposite the side on which the clad layer 32 is provided, and electrodes 391, 392, 393, 394, and 395 that are provided on the surfaces of the contact layer 36 and the insulating layer 37 opposite where the clad layer 35 is disposed. A diffraction grating 30 is provided between the waveguide formation process etching stop layer 34 and the clad layer 35 of the second pulse compression section 7. The waveguide formation process etching stop layer is not limited to being provided directly on the active layer and it is acceptable to provide it, for example, in the clad layer.

While there are no particular limitations on the constituent materials of each section, as an example, the substrate 31 and the contact layer 36 might each be made of GaAs. Meanwhile, the clad layers 32 and 35, the waveguide formation process etching stop layer 34, and the diffraction grating 30 might be made of, for example, AlGaAs. Also, the active layer 33 is made to have, for example, a structure that uses a quantum effect called "multiple quantum well." More specifically, the active layer 33 has, for example, a structure called a distributed refractive index multiple quantum well structure comprising multiple quantum wells obtained by providing well layers (GaAs well layers) and barrier layers (AlGaAs barrier layers) alternately.

In the configuration shown in the figure, the waveguide in the light source device 3a comprises the clad layer 32, the active layer 33, the waveguide forming process etching stop layer 34, and the clad layer 35. The clad layer 35 is provided only on an upper portion of the waveguide and has a shape corresponding to the waveguide. The clad layer 35 is formed by using etching to remove unnecessary portions. Depending on the manufacturing method, it is acceptable to omit the waveguide formation process etching stop layer 34.

Also, two clad layers 35 and two contact layers 36 are provided. One of the clad layers 35 and one of the contact layers 36 are provided in a continuous fashion and constitute the light pulse generator 4, the first pulse compressor 5, the amplifier 6, and a portion of the second pulse compressor 7. The other clad layer 35 and contact layer 36 constitute a portion of the second pulse compressor 7. That is, the pair of clad layers 35 and the pair of contact layers 36 are provided in the second pulse compressor 7.

The electrode 391 is provided to correspond to the clad layer 35 of the light pulse generator 4, the electrode 392 is provided to correspond to the clad layer 35 of the first pulse compressor 5, the electrode 393 is provided to correspond to the clad layer 35 of the amplifier 6, and the electrodes 394 and 395 are provided to correspond, respectively, to the two clad layers 35 of the second pulse compressor 7. The electrode 38 is a common electrode of the light pulse generator 4, the first pulse compressor 5, the amplifier 6, and the second pulse compressor 7. The electrode 38 and the electrode 391 constitute a pair of electrodes for the light pulse generator 4, the electrode 38 and the electrode 392 constitute a pair of electrodes for the first pulse compressor 5, the electrode 38 and the electrode 393 constitute a pair of electrodes for the amplifier 6. Although the overall shape of the light source device 3a is depicted as a rectangular box in the drawings, the invention is clearly not limited to such a shape. Although there are no particular limitations on the dimensions of the light source device 3a, the dimensions can be set such that, for example, one side dimension is equal to or larger than 1 mm and smaller than or equal to 10 mm, another side dimension is equal to or larger than 0.5 mm and smaller than or equal to 5 mm, and the other side dimension is equal to or larger than 0.1 mm and smaller than or equal to 1 mm.

The operation of the terahertz wave generating device 1 will now be explained. In the terahertz wave generating device 1, first a light pulse is generated by the light source generator 4 of each of the light source devices 3a and 3b of the light source unit 10. One of the light source devices 3a will now be explained representatively. The pulse width of the light pulse generated by the light pulse generator 4 is larger than a targeted pulse width. The light pulse generated by light pulse generator 4 passes through the waveguide and then passes successively through the first pulse compressor 5, the amplifier 6, and the second pulse compressor 7.

At the first pulse compressor 5, the light pulse is compressed based on saturable absorption such that the pulse width of the light pulse is decreased. Then, at the amplifier 6, the light pulse is amplified. Finally, at the first pulse compressor 7, the light pulse is compressed based on a group velocity dispersion compensation such that the pulse width of the light pulse is decreased further. A light pulse having the targeted pulse width is generated and emitted from the second pulse compressor 7. Light pulses are emitted from the light source devices 3a and 3b at timings (phases) that are offset from each other.

The light pulses emitted from the light source devices 3a and 3b are irradiated onto the space between the pair of electrodes 22 of the antenna 2 at offset timings (phases) and the antenna 2 generates terahertz waves. As explained previously, the frequency distribution of the terahertz waves can be adjusted by adjusting the amount by which the irradiation timings of the light pulses are offset from each other. Thus, as explained previously, with this terahertz wave generating device 1, the frequency distribution of the terahertz waves can be adjusted easily and reliably.

Since each of the light source devices 3a and 3b has a first pulse compressor 5, an amplifier 6, and a second pulse compressor 7, light pulses having a desired wave height and a desired pulse width can be generated and, thus, the desired terahertz waves can be generated in a reliable manner while making the light source devices 3a and 3b smaller and, thereby, making the terahertz wave generating device 1 smaller. By changing a timing of a drive signal of each of the light source devices 3a and 3b, the light emission timings of the light pulses irradiated from the light source devices 3a and 3b onto the antenna 2 can easily be changed. Thus, it is not necessary to provide a delay device or other additional component to change the timings of the light pulses shown onto the antenna 2 and a simpler configuration can be achieved. The number of light source devices of the light source unit 10 is not limited to two and it is acceptable to provide three or more light source devices. Also, the number of pairs of electrodes 22 of the antenna 2 is not limited to one and it is acceptable to provide two or more pairs.

Second Embodiment

Figure 5:
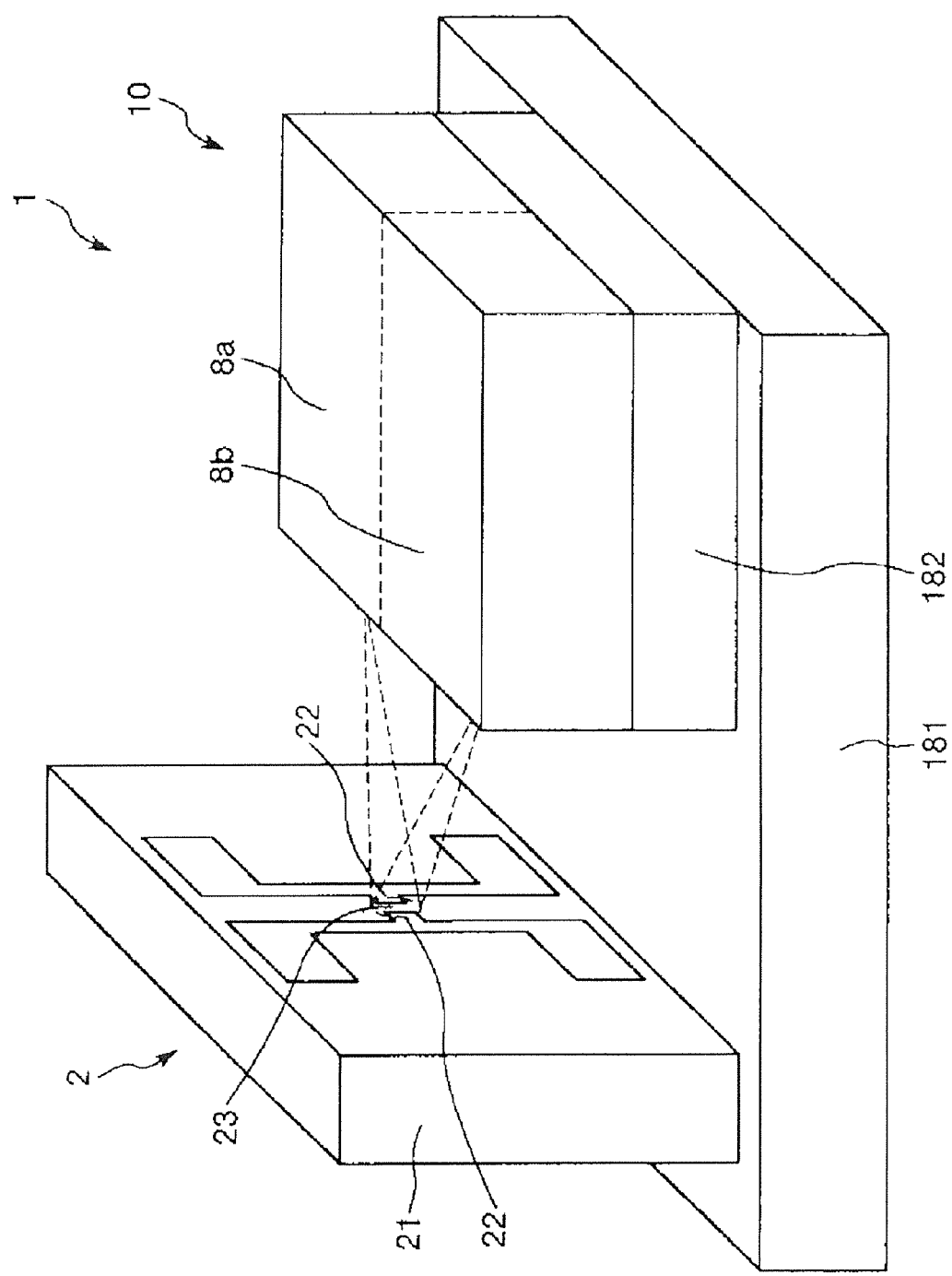
FIG. 5 is a perspective view schematically illustrating a second embodiment of a terahertz wave generating device according to the present invention.
Figure 6:
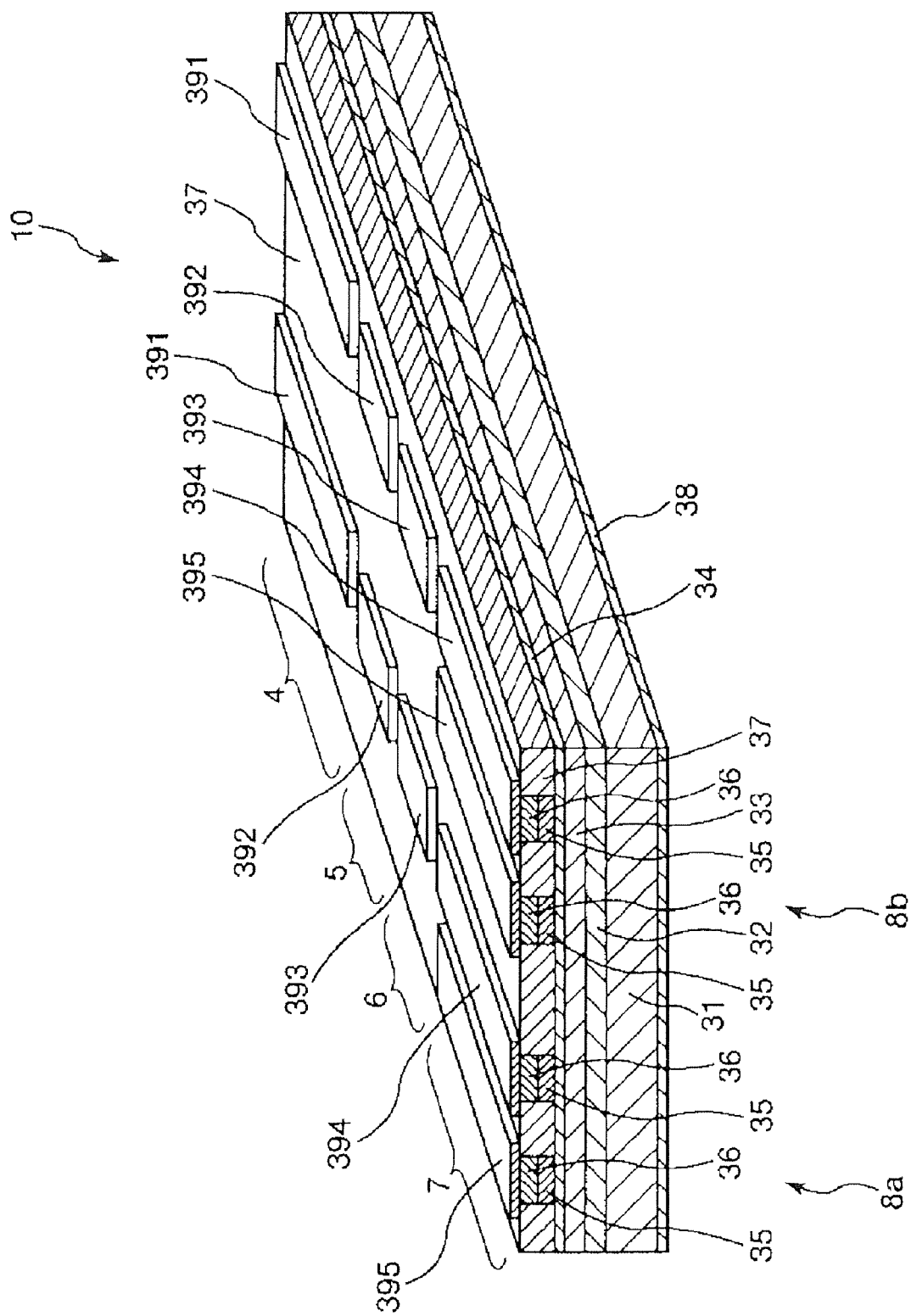
FIG. 6 is a sectional perspective view of a light source device of the terahertz wave generating device shown in FIG. 5.

FIG. 5 is a perspective view schematically illustrating a second embodiment of a terahertz wave generating device according to the present invention, and FIG. 6 is a sectional perspective view of a light source device of the terahertz wave generating device shown in FIG. 5. In FIG. 5, a broken line indicates a border between discrete units 8a and 8b. The second embodiment will be explained focusing on the differences with respect to the previously explained first embodiment and explanations of parts that are the same will be omitted.

As shown in FIGS. 5 and 6, in the terahertz wave generating device 1 of the second embodiment, the light source unit 10 comprises a discrete unit 8a serving as a first light source and a discrete unit 8b serving as a second light source and each of the discrete units has a light pulse generator 4, a first pulse compressor 5, an amplifier 6, and a second pulse compressor 7. These discrete units 8a and 8b are arranged side by side and combined as an integral unit, i.e., an array. As a result, the light source unit 10 can be made smaller and, thus, the terahertz wave generating device 1 can be made smaller. The discrete units 8a and 8b correspond to the light source devices 3a and 3b, respectively, of the previously explained first embodiment. Also, this second embodiment can be employed in the fourth, fifth, and sixth embodiments to be explained later.

Third Embodiment

Figure 7:
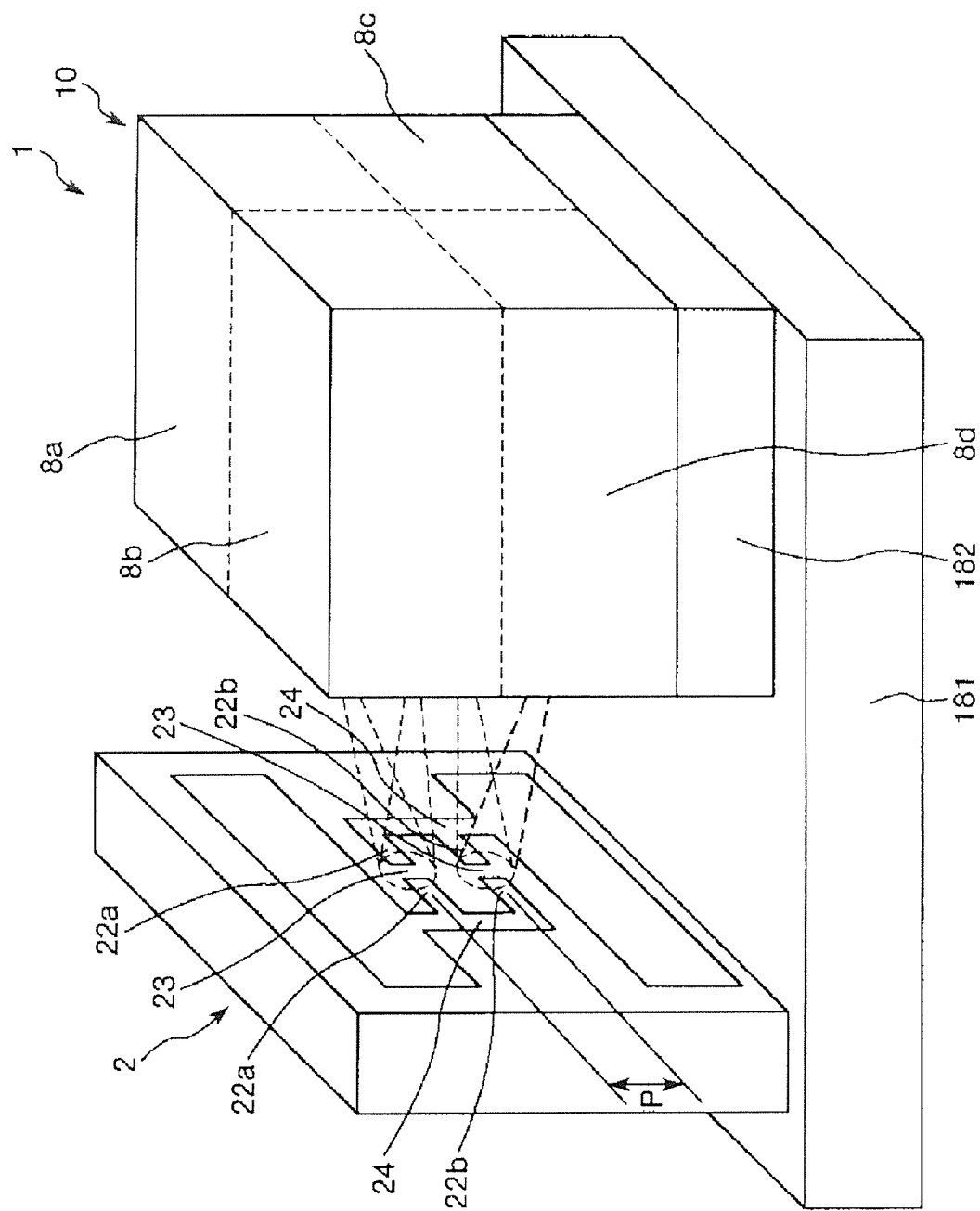
FIG. 7 is a perspective view schematically illustrating a third embodiment of a terahertz wave generating device according to the present invention.

FIG. 7 is a perspective view schematically illustrating a third embodiment of a terahertz wave generating device according to the present invention. In FIG. 7, broken lines indicate borders between discrete units 8a, 8b, 8c, and 8d. The third embodiment will be explained focusing on the differences with respect to the previously explained embodiments and explanations of parts that are the same will be omitted.

As shown in FIG. 7, in the terahertz wave generating device 1 of the third embodiment, the light source unit 10 comprises a discrete unit 8a serving as a first light source, a discrete unit 8b serving as a second light source, a discrete unit 8c serving as a third light source, and a discrete unit 8d serving as a fourth light source. These discrete units 8a, 8b, 8c, 8d are arranged side by side and combined as an integral unit, i.e., an array. As a result, the light source unit 10 can be made smaller and, thus, the terahertz wave generating device 1 can be made smaller. The discrete units 8a and 8b correspond to the discrete units 8a and 8b, respectively, of the second embodiment, and the discrete units 8c and 8d are also the same as the discrete units 8a and 8b. Also, the discrete units 8a and 8b are arranged side by side, and the discrete units 8c and 8d are arranged side by side below the discrete units 8a and 8b.

The antenna 2 comprises a substrate 21 that is a semiconductor substrate, a pair of electrodes 22a that serve as a first pair of electrodes and are provided on the substrate 21 separated by a gap 23, and a pair of electrodes 22b that serve as a second pair of electrodes and are provided on the substrate 21 separated by a gap 23. A prescribed voltage is applied across the pair of electrodes 22a and across the pair of electrodes 22b, and the antenna 2 generates terahertz waves when light pulses are irradiated on the space between the pair of electrodes 22a and the space between the pair of electrode 22b.

In this embodiment, the electrode 22a and the electrode 22b located on one side of each of the pairs, i.e., the electrodes 22a and 22b on one side, are connected together electrically with a conductor 24, and the electrode 22a and the electrode 22b located on the other side of each of the pairs, i.e., the electrodes 22a and 22b on the other side, are connected together electrically with a conductor 24. The same voltage is applied between the electrodes 22a and 22b on one side and between the electrodes 22a and 22b on the other side. That is, a voltage source (not shown in the drawings) is connected between the electrodes 22a and 22b on one side and between the electrodes 22a and 22b on the other side and a prescribed voltage is applied by the voltage source. It is also acceptable to connect separate voltage sources between the pair of electrodes 22a and between the pair of electrodes 22b and apply voltages across the electrodes separately. While there are no particular limitations on a pitch p of the electrodes 22a and 22b and the pitch should be set as appropriate based on various conditions, the pitch p is preferably equal to or larger than 10 μm and smaller than or equal to 1 mm.

In this terahertz wave generating device 1, light pulses are irradiated from the discrete units 8a and 8b of the light source unit 10 onto the space between the common pair of electrodes 22a. Furthermore, the light pulses from the light source unit 10 are irradiated onto the space between the common pair of electrodes 22a at timings, i.e., phases, that are offset from each other. As a result, the frequency distribution of the terahertz waves generated by the antenna 2 is varied in comparison with a case in which the irradiation timings of the light pulses irradiated between the pair of electrodes 22a are not offset or a case in which a light pulse is only irradiated from one of the discrete units 8a or 8b. That is, the frequency distribution of the terahertz waves generated by the antenna 2 can be adjusted.

Similarly, light pulses are irradiated from the discrete units 8c and 8d of the light source unit 10 onto the space between the common pair of electrodes 22b. Furthermore, the light pulses from the light source unit 10 are irradiated onto the space between the common pair of electrodes 22b at timings, i.e., phases, that are offset from each other. As a result, the frequency distribution of the terahertz waves generated by the antenna 2 is varied in comparison with a case in which the irradiation timings of the light pulses irradiated between the pair of electrodes 22b are not offset or a case in which a light pulse is only irradiated from one of the discrete units 8c or 8d. That is, the frequency distribution of the terahertz waves generated by the antenna 2 can be adjusted.

The frequency distribution of the terahertz waves is adjusted by adjusting the irradiation timing offset amount of the light pulses irradiated between the pair of electrodes 22a and the irradiation timing offset amount of the light pulses irradiated between the pair of electrodes 22b or by adjusting the irradiation timing offset amount of the light pulses irradiated between the pair of electrodes 22a, the irradiation timing offset amount of the light pulses irradiated between the pair of electrodes 22b, and the ratios $\alpha 1/\alpha 2$.

The adjustment of the frequency distribution of the terahertz wave generating device 1 can be accomplished by experimentally determining a computational formula, table, or other form of analytical curve indicating the relationships between the offset amounts of the irradiation timings and the frequency distributions of the terahertz waves or a computational formula, table, or detection amount indicating the relationships among the offset amounts of the irradiation timings, the ratios $\alpha 1/\alpha 2$, and the frequency distributions of the terahertz waves and storing the analytical curve in a memory section (not shown) of the terahertz wave generating device 1. When necessary, the stored data is read and used.

Additionally, in this terahertz wave generating apparatus 1, the light pulses irradiated from the light source unit 10 onto the space between the pair of electrodes 22a and the light pulses irradiated from the light source unit 10 onto the space between the electrodes 22b are irradiated with timings, i.e., phases, that are offset from each other. That is, at least one of the light pulses emitted from the discrete unit 8a and the light pulses emitted from the discrete unit 8b has a different phase than at least one of the light pulses emitted from the discrete unit 8c and the light pulses emitted from the discrete unit 8d. In this embodiment, the phases of the light pulses emitted from the discrete unit 8a and the light pulses emitted from the discrete unit 8c are different, and the phases of the light pulses emitted from the discrete unit 8b and the light pulses emitted from the discrete unit 8d are different. As a result, the terahertz waves generated between the pair of electrodes 22a and the terahertz waves generated between the pair of electrodes 22b have different phases and by combining these terahertz waves, the emission direction of the terahertz waves generated by the antenna 2 is changed in comparison with a situation in which the irradiation timings of the light pulses are not offset from each other. That is, the emission direction of the terahertz waves generated by the antenna 2 can be adjusted.

Also, there are no particular limitations on the amount by which the light pulses emitted from the discrete unit 8a and irradiated on the space between the pair of electrodes 22a are offset from the light pulses emitted from the discrete unit 8c and irradiated on the space between the pair of electrodes 22b and the amount by which the light pulses emitted from the discrete unit 8b and irradiated on the space between the pair of electrodes 22a are offset from the light pulses emitted from the discrete unit 8d and irradiated on the space between the pair of electrodes 22b. Although the offset amounts are set as appropriate based on the targeted emission direction of the terahertz waves to be generated and various other conditions, the offset amount is preferably smaller than the pulse width of the light pulses. More specifically, the offset amount of the irradiation timings of the light pulses is preferably set to an amount equal to or larger than 1% and smaller than or equal to 50% of the pulse width of the light pulses, and still more preferably set to an amount equal to or larger than 3% and smaller than or equal to 40% of the pulse width of the light pulses.

By adjusting the offset amounts of the irradiation timings of the light pulses irradiated between the pair of electrodes 22a and between the pair of electrodes 22b, the emission direction of the terahertz waves can be adjusted. The adjustment of the emission direction of the terahertz wave generating device 1 can be accomplished by experimentally determining in advance a computational formula, table, or other form of analytical curve indicating a relationship between the offset amount of the irradiation timings and the emission direction of the terahertz waves and storing the analytical curve in a memory section (not shown) of the terahertz wave generating device 1. When necessary, the stored data is read and used.

As explained previously, with this terahertz wave generating device 1, the frequency distribution of the terahertz waves can be adjusted easily and reliably and an emission direction of the terahertz waves can be changed. The number of discrete units (light source devices) of the light source unit 10 is not limited to four and it is acceptable to provide five or more. Also, the number of pairs of electrodes 22 of the antenna 2 is not limited to two and it is acceptable to provide three or more pairs. Also, this third embodiment can be employed in the fourth, fifth, and sixth embodiments to be explained later.

Fourth Embodiment

Figure 8:
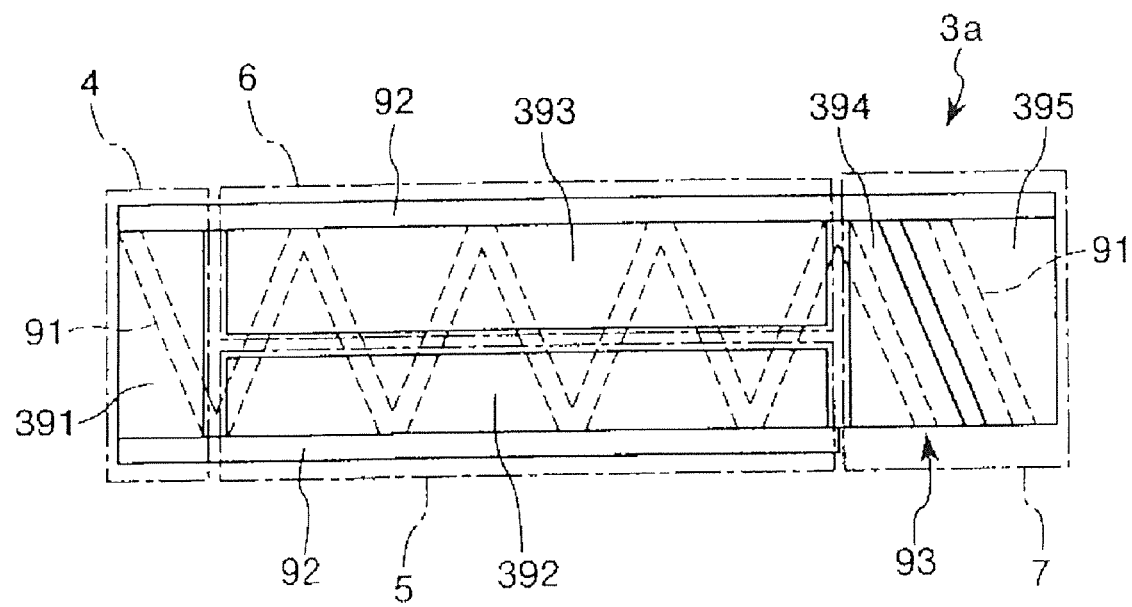
FIG. 8 is a plan view schematically illustrating a light source device in a fourth embodiment of a terahertz wave generating device according to the present invention.

FIG. 8 is a plan view schematically illustrating a light source device in a fourth embodiment of a terahertz wave generating device according to the present invention. In FIG. 8, a broken line indicates a waveguide 91 and each of the first pulse compressor 5, the amplifier 6, and the second pulse compressor 7 is enclosed inside a broken line. The fourth embodiment will be explained focusing on the differences with respect to the previously explained embodiments and explanations of parts that are the same will be omitted.

As shown in FIG. 8, in the fourth embodiment, the waveguide of the light source device 3a of the terahertz wave generating device 1 is folded alternately several times. That is, the wave guide 91 is configured to zigzag. The first pulse compressor 5 is positioned underneath from the perspective of FIG. 8, and the amplifier is positioned above from the perspective of FIG. 8. The waveguide 91 is folded several times in each of the first pulse compressor 5 and the amplifier 6. The waveguide 91 is also folded once at a border portion between the light pulse generator 4 and the first pulse compressor 5 and once at a border portion between the amplifier 6 and the second pulse compressor 7.

The light source device 3a has reflective films 92 that reflects light pulses provided on a folded portion of the waveguide 91. The reflective films 92 are provided on a pair of side faces of the light source device. The reflective films 92 can reflect a light pulse such that the light pulse proceeds along the waveguide 91. The reflective films 92 are not provided on a light pulse emitter 93 of the light source device 3a. It is also acceptable to provide an antireflective film (not shown in the drawings) on the emitter 93. With this terahertz wave generating device 1, since the waveguide 91 of the light emitting device 3a is folded several times, the optical path length, i.e., the linear length of the waveguide 91, can be made longer. As a result, the length of the light source device 3a can be shortened and the size can be decreased further.

Fifth Embodiment

Figure 9:
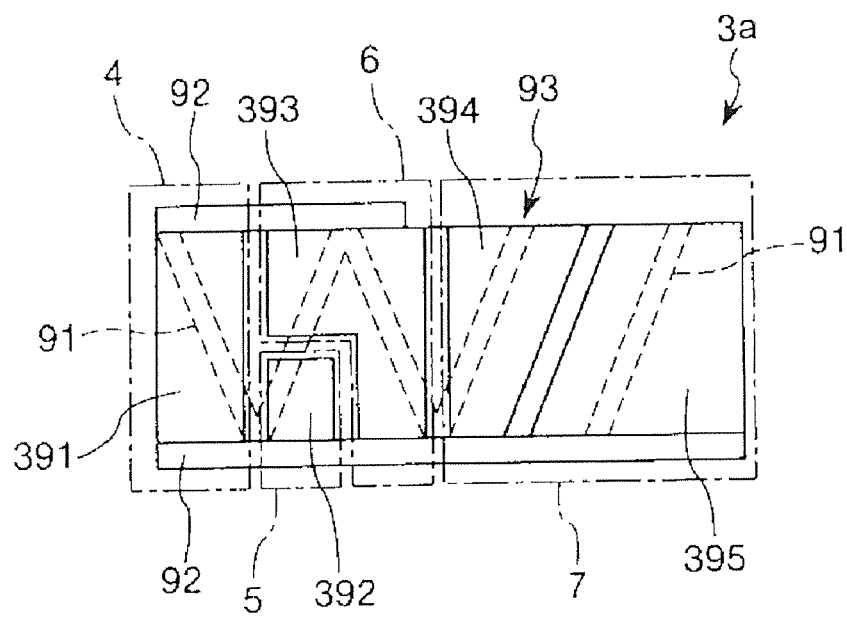
FIG. 9 is a plan view schematically illustrating a light source device in a fifth embodiment of a terahertz wave generating device according to the present invention.

FIG. 9 is a plan view schematically illustrating a light source device in a fifth embodiment of a terahertz wave generating device according to the present invention. In FIG. 9, a broken line indicates a waveguide and each of the first pulse compressor 5, the amplifier 6, and the second pulse compressor 7 is enclosed inside a broken line.

The fifth embodiment will be explained focusing on the differences with respect to the previously explained embodiments and explanations of parts that are the same will be omitted. As shown in FIG. 9, in the light source device 3a of the terahertz wave generating device 1 of the fifth embodiment, the waveguide 91 is folded alternately three times, and the waveguide 91 is folded only once in the amplifier 6. However, if the amplifier 6 is provided at upstream of the first pulse compressor 5, then the waveguide 91 will be folded only once in the first pulse compressor 5.

Sixth Embodiment

Figure 10:
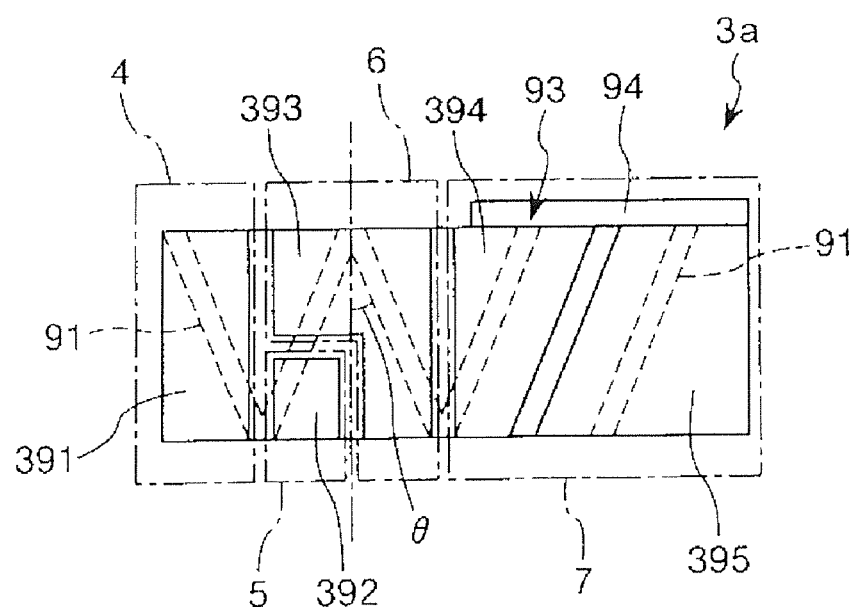
FIG. 10 is a plan view schematically illustrating a light source device in a sixth embodiment of a terahertz wave generating device according to the present invention.

FIG. 10 is a plan view schematically illustrating a light source device in a sixth embodiment of a terahertz wave generating device according to the present invention. In FIG. 10, a broken line indicates a waveguide and each of the first pulse compressor 5, the amplifier 6, and the second pulse compressor 7 is enclosed inside a broken line. The sixth embodiment will be explained focusing on the differences with respect to the previously explained embodiments and explanations of parts that are the same will be omitted.

As shown in FIG. 10, in the sixth embodiment, the reflective films 92 are omitted from the light source device 3a of the terahertz wave generating device 1. Also, an angle θ at a folded portion of the waveguide 91 shown in FIG. 10 is set to be equal to or larger than a critical angle. As a result, a light pulse can be reflected without providing reflective films 92 at the folded portions of the waveguide 91 and the structure can be simplified. Meanwhile, an antireflective film 94 is provided on a light pulse emitter 93 of the light source device 3a. As a result, light pulses can be emitted from the emitter 93. The sixth embodiment can also be employed in the fourth embodiment.

Embodiment of Imaging Device

Figure 11:
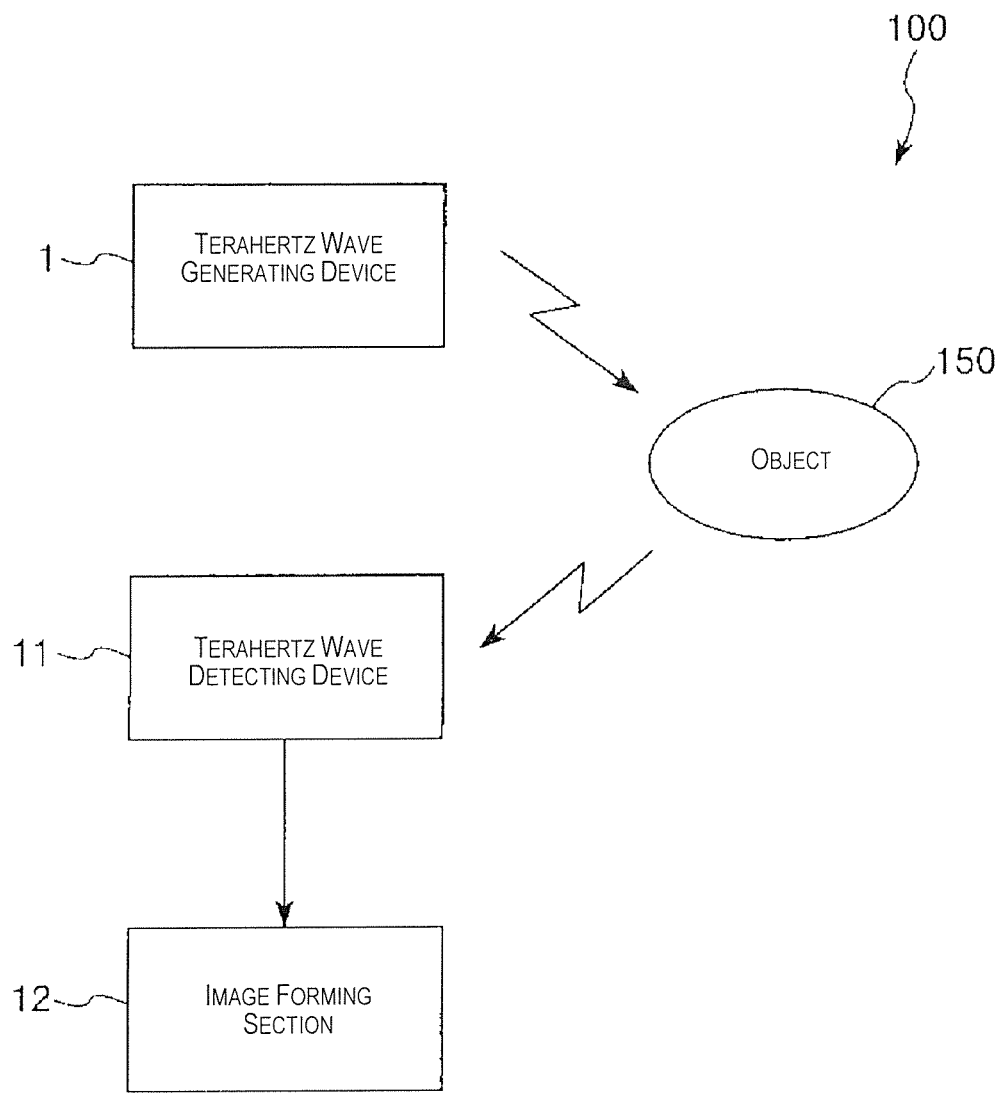
FIG. 11 is a block diagram showing an embodiment of an imaging device according to the present invention.
Figure 12:
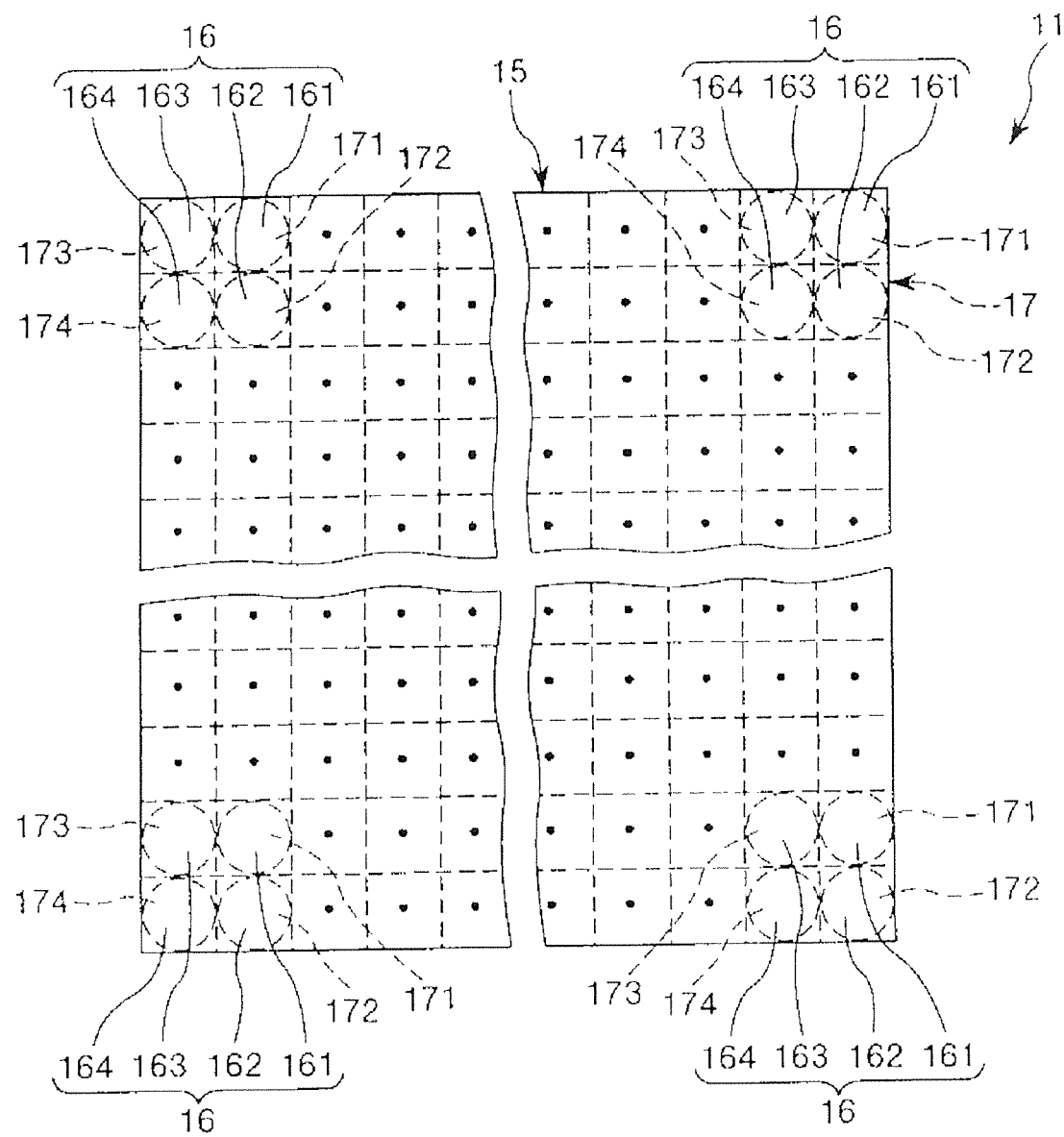
FIG. 12 is a plan view of a terahertz wave detecting device of the imaging device shown in FIG. 11.

FIG. 11 is a block diagram showing an embodiment of an imaging device according to the present invention. FIG. 12 is a plan view of a terahertz wave detecting device of the imaging device shown in FIG. 11. As shown in FIG. 11, the imaging device 100 comprises a terahertz wave generating device 1 that generates terahertz waves, a terahertz wave detecting device 11 that detects terahertz waves that have been emitted from the terahertz wave generating device 1 and have penetrated through or been reflected from an object 150, and an image forming section 12 that produces an image, i.e., image data, of the object 150 based on a detection result of the terahertz wave detecting device 11.

In this embodiment, the terahertz wave generating device 1 is a terahertz wave generating device according to any one of the first to sixth embodiments. The terahertz wave detecting device 11 comprises, for example, a filter 15 that passes terahertz waves of a targeted wavelength and a detecting section 17 that detects terahertz waves of the targeted wavelength that have passed through the filter 15 by converting the terahertz waves into heat. The detecting section 17 is configured to, for example, detect a terahertz wave by converting it into heat, i.e., by converting the terahertz wave into heat and detecting the energy (intensity) of the terahertz wave. Examples of such a detecting section include a pyroelectric sensor and a bolometer. Needless to say, the terahertz wave detecting device 11 is not limited to the configuration just explained.

The filter 15 has a plurality of pixels (unit filter sections) 16 arranged two-dimensionally. That is, the pixels 16 are arranged in a matrix format. Each of the pixels 16 has a plurality of regions that pass terahertz waves having different wavelengths, i.e., a plurality of regions configured such that the wavelength of terahertz wave that passes through (hereinafter called "transmission wavelength") each of the regions is different. Also, in the configuration shown in the drawing, each of the pixels 16 has a first region 161, a second region 162, a third region 163, and a fourth region 164.

The detecting section 17 has a first discrete detector 171, a second discrete detector 172, a third discrete detector 173, and a fourth discrete detector 174 each corresponding, respectively, to the first region 161, the second region 162, the third region 163, and the fourth region 164 of each of the pixels 16 of the filter 15. The first discrete detectors 171, the second discrete detectors 172, the third discrete detectors 173, and the fourth discrete detectors 174 detect terahertz waves that pass through the first regions 161, the second regions 162, the third regions 163, and the fourth regions 164 by converting the terahertz waves into heat. In this way, four targeted wavelengths of terahertz wave can be detected reliably at each of the pixels 16.

The operation of the imaging device 100 will now be explained. An object 150 subjected to spectral imaging is made of three substances A, B, and C. The image device 100 executes spectral imaging of this object 150. In this explanation, as an example, it will be assumed that the terahertz wave generating device 11 detects terahertz waves reflected from the object 150.

Figure 13:
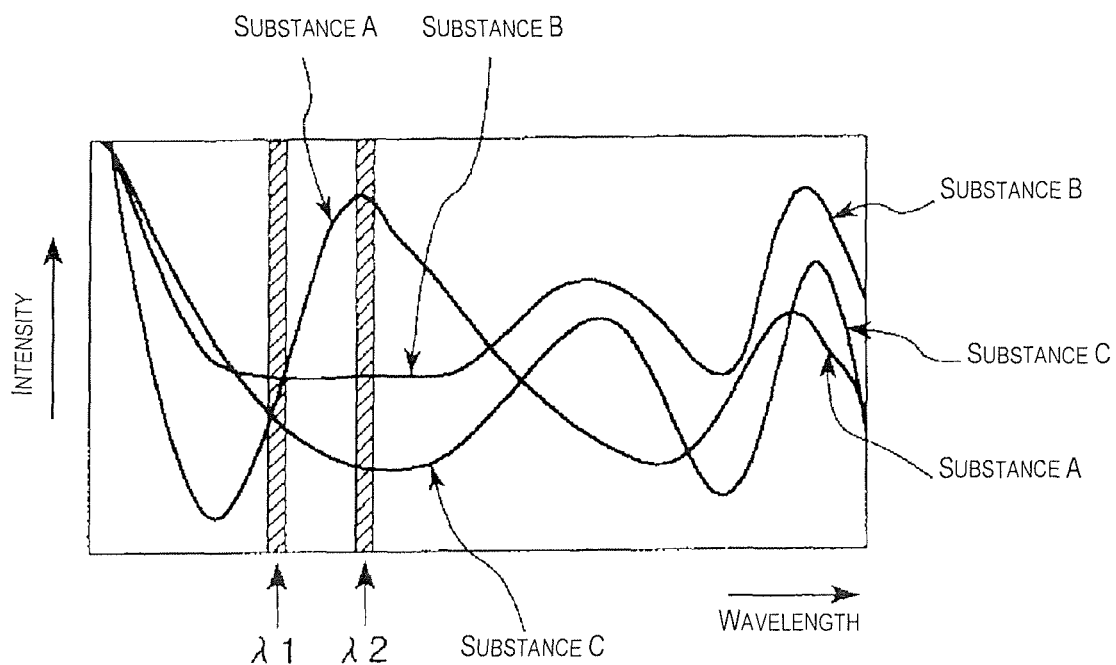
FIG. 13 is a graph showing a spectrum of an object in the terahertz band.

FIG. 13 is a graph showing a spectrum of the object 150 in the terahertz band. The terahertz wave detecting device 11 uses the first region 161 and the second region 162 at each pixel 16 of the filter 15. Assuming the first regions 161 have a transmission wavelength λ1, the second regions 162 have a transmission wavelength λ2, the wavelength λ1 component of the terahertz waves reflected from the object 150 has an intensity α1, and the wavelength λ2 component of the same has an intensity α2, then the transmission wavelength λ1 of the first regions 161 and the transmission wavelength λ2 of the second regions 162 are set such that a difference between the intensities α2 and α1 (α2−α1) can be clearly distinguished among the substance A, the substance B, and the substance C.

As shown in FIG. 13, the difference (α2−α1) between the intensity α2 of the wavelength λ2 component and the intensity α1 of the wavelength 21 component of the terahertz waves reflected from the object 150 is a positive value for the substance A. Meanwhile, the difference (α2−α1) between the intensity α2 and the intensity α1 is zero for the substance B, and the difference (α2−α1) between the intensity α2 and the intensity α1 is a negative value for the substance C.

When the imaging device 100 executes spectral imaging of the object 150, first the terahertz wave generating device 1 generates terahertz waves and irradiates the object 150 with the terahertz waves. Terahertz waves reflected from the object 150 are then detected by the terahertz wave detecting device 11 in terms of the intensities α1 and α2. The detection results are sent to the image forming section 12. This process of irradiating the object 150 with terahertz waves and detecting the terahertz waves reflected from the object 150 is conducted with respect to the entire object 150. During this irradiation of the object 150 with terahertz waves, the light source unit 10 irradiates the light pulses between the pairs of electrodes 22 at timings that are offset from each other and the direction in which the terahertz waves are emitted is varied by varying the amount by which the irradiation timings of the light pulses are offset from each other.

Based on the detection results, the image forming section 12 finds the difference ($\alpha 2-\alpha 1$) between the intensity $\alpha 2$ of the wavelength $\lambda 2$ component of the terahertz waves transmitted through the second regions 162 of the filter 15 and the intensity $\alpha 1$ of the wavelength $\lambda 1$ component of the terahertz waves transmitted through the first regions 161. Then, parts of the object 150 where the difference is positive are identified as the substance A, parts where the difference is zero are identified as the substance B, and parts where the difference is negative are identified as the substance C.

Figure 14:
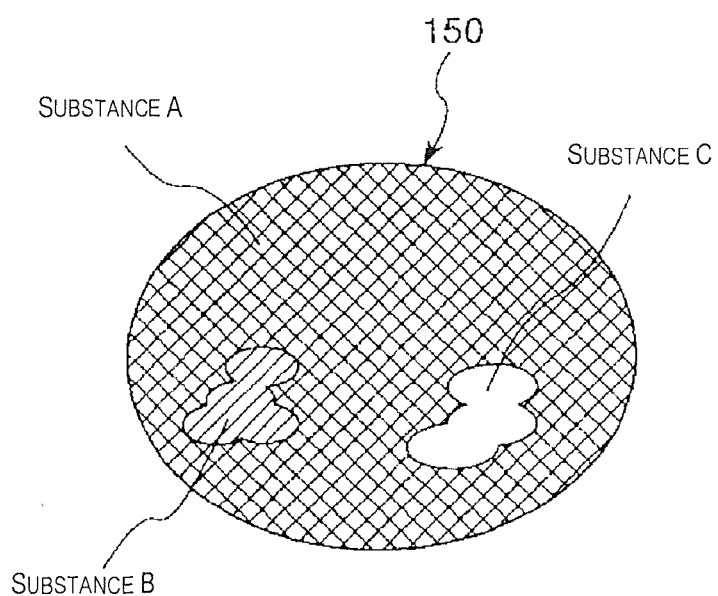
FIG. 14 is an image showing a distribution of substances A, B, and C of the object.

As shown in FIG. 14, the image forming section 12 creates image data of an image indicating a distribution of the substances A, B, and C in the object 150. This image data is sent from the image forming section 12 to a monitor not shown in the drawings, and an image indicating the distribution of the substances A, B, and C in the object 150 is displayed on the monitor. This displayed image is, for example, color coded such that a region of the object 150 where the substance A is distributed is indicated in black, a region where the substance B is distributed is indicated in gray, and a region of where the substance C is distributed is indicated in white. As explained previously, with this imaging device 100, it is possible to identify each of the substances making up the object 150 and also, simultaneously, to measure the distribution of each of the substances. The application of the imaging device 100 is not limited to the application just explained. For example, it is also possible to irradiate a person with terahertz waves, detect terahertz waves that have penetrated through or been reflected from the person, and use the image forming section 12 to process the detection results in order to determine if the person is carrying a handgun, a knife, an illegal drug, or the like.

Embodiment of Measuring Device

Figure 15:
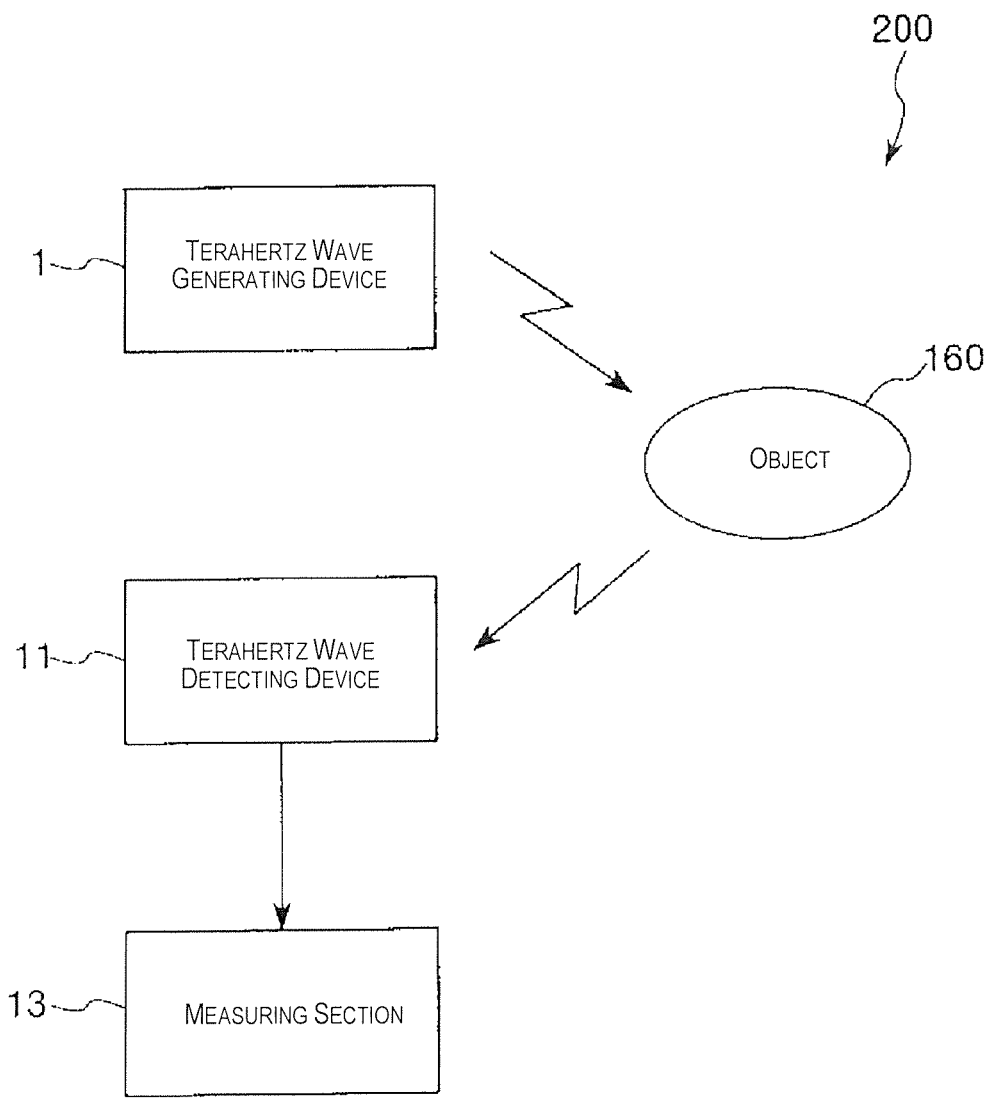
FIG. 15 is a block diagram showing an embodiment of a measuring device according to the present invention.

FIG. 15 is a block diagram showing an embodiment of a measuring device according to the present invention. The embodiment of the measuring device will be explained focusing on the differences with respect to the previously explained embodiment of the imaging device and explanations of parts that are the same will be omitted. As shown in FIG. 15, the measuring device 200 comprises a terahertz wave generating device 1 that generates terahertz waves, a terahertz wave detecting device 11 that detects terahertz waves that have been emitted from the terahertz wave generating device 1 and have penetrated through or been reflected from an object 160, and a measuring section 13 that measures the object 160 based on a detection result of the terahertz wave detecting device 11.

An example of using the measuring device 200 will now be explained.

When the measuring device 200 executes spectrometry of the object 160, first the terahertz wave generating device 1 generates terahertz waves and irradiates the object 160 with the terahertz waves. Then the terahertz detecting device 11 detects terahertz waves that have penetrated through or been reflected off the object 160. The detection results are sent to the measuring section 13. This process of irradiating the object 160 with terahertz waves and detecting the terahertz waves that penetrate through or reflect from the object 160 is conducted with respect to the entire object 160. During this irradiation of the object 160 with terahertz waves, the light source unit 10 irradiates the light pulses between the pairs of electrodes 22 at timings that are offset from each other and the direction in which the terahertz waves are emitted is varied by varying the amount by which the irradiation timings of the light pulses are offset from each other. Based on the detection results, the measuring section 13 determines the intensities of the terahertz waves passing through each of the first regions 161, the second regions 162, the third regions 163, and the fourth regions 164 of the filter 15 and executes analyses of the components of the object 160 and the distribution of the components.

Embodiment of Camera

Figure 16:
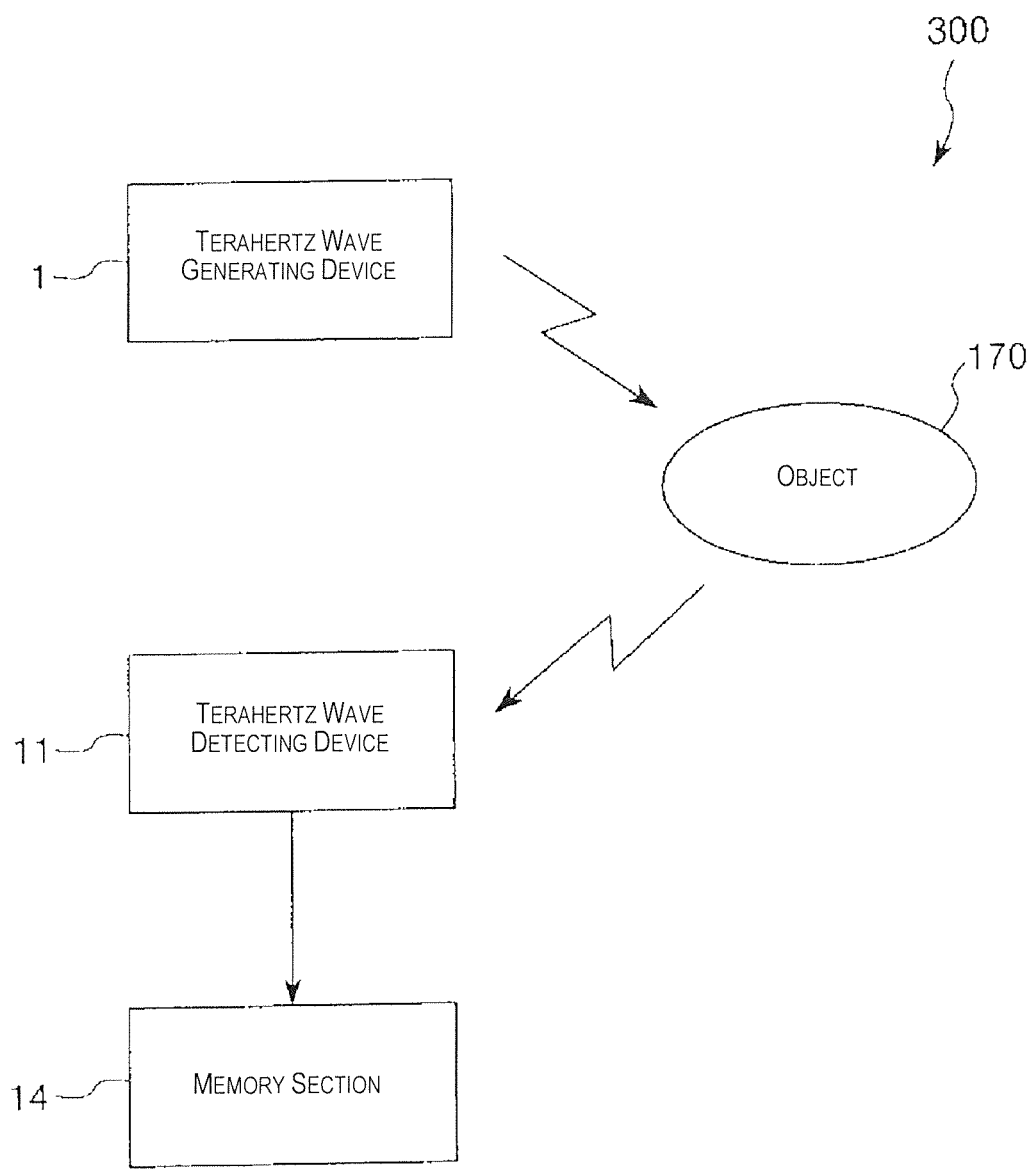
FIG. 16 is a block diagram showing an embodiment of a camera according to the present invention.

FIG. 16 is a block diagram showing an embodiment of a camera according to the present invention. The embodiment of the camera will be explained focusing on the differences with respect to the previously explained embodiment of the imaging device and explanations of parts that are the same will be omitted. As shown in FIG. 16, the camera 300 comprises a terahertz wave generating device 1 that generates terahertz waves and a terahertz wave detecting device 11 that detects terahertz waves that have been emitted from the terahertz wave generating device 1 and have penetrated through or been reflected from an object 170.

An example of using the camera 300 will now be explained. When the camera 300 photographs the object 170, first the terahertz wave generating device 1 generates terahertz waves and irradiates the object 170 with the terahertz waves. Then the terahertz detecting device 11 detects terahertz waves that have penetrated through or been reflected by the object 170. The detection results are sent to a memory section 14 and stored. This process of irradiating the object 170 with terahertz waves and detecting the terahertz waves that have penetrated through or been reflected from the object 170 is conducted with respect to the entire object 170. During this irradiation of the object 170 with terahertz waves, the light source unit 10 irradiates the light pulses between the pairs of electrodes 22 at timings that are offset from each other and the direction in which the terahertz waves are emitted is varied by varying the amount by which the irradiation timings of the light pulses are offset from each other. The detection results can also be sent to, for example, a personal computer or other external device. With a personal computer, various processing can be executed based on the detection results.

Although a terahertz wave generating device, a camera, an imaging device, and a measuring device according to the present invention are explained herein based on the embodiments depicted in the drawings, the present invention is not limited to these embodiments and any of the constituent parts can be replaced with other constituent parts having the same functions. It is also acceptable to add other constituent parts to the present invention as desired. Also, in the present invention, it is acceptable to combine two or more constituent parts (features) of the different embodiments as desired. In the present invention, it is also acceptable if the light pulse generator is provided separately from the light source device (light source unit).

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A terahertz wave generating device comprising:
    a first light source and a second light source configured and arranged to generate pulsed lights; and
    an antenna configured and arranged to generate terahertz waves when irradiated by the pulsed lights generated by the first light source and the second light source, the antenna having a pair of electrodes arranged opposite each other with a gap being formed therebetween,
    the first light source irradiating first pulsed lights,
    the second light source irradiating second pulsed lights,
    the first pulsed lights and the second pulsed lights being incident to the antenna at different directions, and
    the first light source and the second light source being configured and arranged to irradiate the pulsed lights between the electrodes at timings that are offset from each other.

2. The terahertz wave generating device according claim 1, wherein
    an amount by which irradiation timings of the pulsed lights are offset from each other is smaller than a pulse width of each of the pulsed lights.

3. The terahertz wave generating device according to claim 1, wherein
    each of the first light source and the second light source is a semiconductor laser.

4. The terahertz wave generating device according to claim 1, wherein
    the first light source and the second light source are provided as an integral unit.

5. A terahertz wave generating device comprising:
    a first light source, a second light source, a third light source, and a fourth light source configured and arranged to generate pulsed lights; and
    an antenna configured and arranged to generate terahertz waves when irradiated by the pulsed lights generated by the first light source, the second light source, the third light source, and the fourth light source, the antenna having a first pair of electrodes and a second pair of electrodes, the electrodes of each of the first and second pairs being arranged opposite each other with a gap being formed therebetween,
    the first light source irradiating first pulsed lights,
    the second light source irradiating second pulsed lights,
    the first pulsed lights and the second pulsed lights being incident to the antenna at different directions,
    the third light source irradiating third pulsed lights,
    the fourth light source irradiating fourth pulsed lights,
    the third pulsed lights and the fourth pulsed lights being incident to the antenna at different directions,
    the first light source and the second light source being configured and arranged to irradiate the pulsed lights between the electrodes of the first pair at timings that are offset from each other,
    the third light source and the fourth light source being configured and arranged to irradiate the pulsed lights between the electrodes of the second pair at timings that are offset from each other, and
    a phase of at least one of the pulsed light emitted from the first light source and the pulsed light emitted from the second light source and a phase of at least one of the pulsed light emitted from the third light source and the pulsed light emitted from the fourth light source are different.

6. The terahertz wave generating device according to claim 5, wherein
    an amount by which irradiation timings of the pulsed lights irradiated between the electrodes of the first pair are offset from each other is smaller than a pulse width of each of the pulsed lights, and
    an amount by which irradiation timings of the pulsed lights irradiated between the electrodes of the second pair are offset from each other is smaller than a pulse width of each of the pulsed lights.

7. The terahertz wave generating device according to claim 5, wherein
    an amount of offset between the phase of the least one of the pulsed light emitted from the first light source and the pulsed light emitted from the second light source and the phase of the at least one of the pulsed light emitted from the third light source and the pulsed light emitted from the fourth light source is smaller than a pulse width of each of the pulsed lights.

8. The terahertz wave generating device according to claim 5, wherein
    each of the first light source, the second light source, the third light source, and the fourth light source is a semiconductor laser.

9. The terahertz wave generating device according to claim 5, wherein
    the first light source, the second light source, the third light source, and the fourth light source are provided as an integral unit.

10. The terahertz wave generating device according to claim 5, wherein
    one of the electrodes of the first pair and one of the electrodes of the second pair are electrically connected.

11. A camera comprising:
    a terahertz wave generating device configured and arranged to generate terahertz waves; and
    a terahertz wave detecting device configured and arranged to detect the terahertz waves that have been emitted from the terahertz wave generating device and have penetrated through or been reflected from an object,
    the terahertz wave generating device including
    a first light source and a second light source configured and arranged to generate pulsed lights, and
    an antenna configured and arranged to generate the terahertz waves when irradiated by the pulsed lights generated by the first light source and the second light source, the antenna having a pair of electrodes arranged opposite each other with a gap being formed therebetween,
    the first light source irradiating first pulsed lights, the second light source irradiating second pulsed lights, the first pulsed lights and the second pulsed lights being incident to the antenna at different directions, and the first light source and the second light source being configured and arranged to irradiate the pulsed lights between the electrodes at timings that are offset from each other.

12. An imaging device comprising:

a terahertz wave generating device configured and arranged to generate terahertz waves;

a terahertz wave detecting device configured and arranged to detect the terahertz waves that have been emitted from the terahertz wave generating device and have penetrated through or been reflected from an object; and an image forming section configured and arranged to form an image of the object based on a detection result of the terahertz wave detecting device, the terahertz wave generating device including a first light source and a second light source configured and arranged to generate pulsed lights, and an antenna configured and arranged to generate the terahertz waves when irradiated by the pulsed lights generated by the first light source and the second light source, the antenna having a pair of electrodes arranged opposite each other with a gap being formed therebetween, the first light source irradiating first pulsed lights, the second light source irradiating second pulsed lights, the first pulsed lights and the second pulsed lights being incident to the antenna at different directions, and the first light source and the second light source being configured and arranged to irradiate the pulsed lights between the electrodes at timings that are offset from each other.

13. A measuring device comprising:

a terahertz wave generating device configured and arranged to generate terahertz waves;

a terahertz wave detecting device configured and arranged to detect the terahertz waves that have been emitted from the terahertz wave generating device and have penetrated through or been reflected from an object; and a measuring section configured and arranged to measure the object based on a detection result of the terahertz wave detecting device, the terahertz wave generating device including a first light source and a second light source configured and arranged to generate pulsed lights, and an antenna configured and arranged to generate the terahertz waves when irradiated by the pulsed lights generated by the first light source and the second light source, the antenna having a pair of electrodes arranged opposite each other with a gap being foamed therebetween, the first light source irradiating first pulsed lights, the second light source irradiating second pulsed lights, the first pulsed lights and the second pulsed lights being incident to the antenna at different directions, and the first light source and the second light source being configured and arranged to irradiate the pulsed lights between the electrodes at timings that are offset from each other.

* * * * *